(12) United States Patent
Kikuchi et al.

(10) Patent No.: US 7,794,759 B2
(45) Date of Patent: Sep. 14, 2010

(54) CELL ACTIVATOR, COLLAGEN PRODUCTION PROMOTER, SKIN WHITENING AGENT, ANTIOXIDANT AGENT, ANTIINFLAMMATORY AGENT, AROMATASE ACTIVITY PROMOTER, PROTEASE ACTIVITY PROMOTER, EXTERNAL PREPARATION FOR SKIN, AND FOOD

(75) Inventors: Hiroko Kikuchi, Tokyo (JP); Masaki Arashima, Kobe (JP); Sayaka Aramaki, Kobe (JP); Hiroko Yoshida, Kobe (JP)

(73) Assignee: Noevir Co., Ltd., Hyogo (JP)

( * ) Notice: Subject to any disclaimer, the term of this patent is extended or adjusted under 35 U.S.C. 154(b) by 16 days.

(21) Appl. No.: 12/373,725

(22) PCT Filed: Sep. 4, 2007

(86) PCT No.: PCT/JP2007/067203

§ 371 (c)(1),
(2), (4) Date: Jan. 13, 2009

(87) PCT Pub. No.: WO2008/029798

PCT Pub. Date: Mar. 13, 2008

(65) Prior Publication Data

US 2009/0280197 A1   Nov. 12, 2009

(30) Foreign Application Priority Data

Sep. 6, 2006   (JP) ............................ P2006-242067

(51) Int. Cl.
*A61K 36/00* (2006.01)
(52) U.S. Cl. ...................................... 424/725; 424/401
(58) Field of Classification Search ...................... None
See application file for complete search history.

(56) References Cited

FOREIGN PATENT DOCUMENTS

| | | |
|---|---|---|
| EP | 425398 | 5/1991 |
| JP | 58-88305 | 5/1983 |
| JP | H6-009391 | 1/1994 |
| JP | 6-24937 | 2/1994 |
| JP | 9-295928 | 11/1997 |
| JP | H10-182413 | 7/1998 |
| JP | H10-203952 | 8/1998 |
| JP | 11-349469 | 12/1999 |
| JP | 2000-7545 | 1/2000 |
| JP | 2000-95663 | 4/2000 |
| JP | 2000-154134 | 6/2000 |
| JP | 2000-169321 | 6/2000 |
| JP | 2000-239164 | 9/2000 |
| JP | 2001-131045 | 5/2001 |
| JP | 2003-089630 | 3/2003 |
| JP | 2003-171300 | 6/2003 |
| JP | 2003-226613 | 8/2003 |
| JP | 2004-189609 | 7/2004 |
| JP | 2004-346006 | 12/2004 |
| JP | 2005-112742 | 4/2005 |
| JP | 2006-199678 | 8/2006 |

OTHER PUBLICATIONS

Takushi (Bull. Fac. Sci. Univ. Ryukyus (2003), vol. 75, pp. 13-17).*
Japanese Patent Office, International Search Report for PCT/JP2007/067203, Nov. 6, 2007 (2 pages).
International Preliminary Report on Patentability for PCT/JP2007/067203, Issued Mar. 17, 2009 (5 pages).

* cited by examiner

*Primary Examiner*—Susan C Hoffman
(74) *Attorney, Agent, or Firm*—Squire, Sanders & Dempsey, L.L.P.

(57) ABSTRACT

The present invention provides a cell activation agent, a collagen production accelerator, a whitening agent, an antioxidant, an anti-inflammatory agent, an aromatase activity accelerator, a protease activity accelerator, a skin external preparation, and food, which all contain an extract of *Hibiscus makinoi*.

9 Claims, No Drawings

CELL ACTIVATOR, COLLAGEN PRODUCTION PROMOTER, SKIN WHITENING AGENT, ANTIOXIDANT AGENT, ANTIINFLAMMATORY AGENT, AROMATASE ACTIVITY PROMOTER, PROTEASE ACTIVITY PROMOTER, EXTERNAL PREPARATION FOR SKIN, AND FOOD

TECHNICAL FIELD

The present invention relates to a cell activation agent, a collagen production accelerator, a whitening agent, an antioxidant, an anti-inflammatory agent, an aromatase activity accelerator, a protease activity accelerator, a skin external preparation, and food, which contain an extract of *Hibiscus makinoi*.

BACKGROUND ART

Factors of aging symptoms such as reduction in elasticity of a skin, wrinkles, spots accompanying with aging include lowering of cell functions, decrease and modification of extracellular matrix components such as collagen, production of melanin and pigmentation due to an ultraviolet ray, oxidation damage of cells, and the like. In order to prevent and improve such aging symptoms, conventionally, searches and studies on blending various active ingredients have been made. There are known active ingredients such as an essence of *Citrus reticulate* as a cell activation agent (see Patent Document 1), an extract from a bud of a tree of the family Fagaceae, genus *Fagus* as a collagen production accelerator (see Patent Document 2), water and/or an organic solvent extract of *Rhinacanthus Nasutus* (L.) Kurz as a whitening agent (see Patent Document 3), an extract of a plant of the family Usneaceae, genus *Usnea* as an antioxidant (see Patent Document 4), tea polyphenols as an anti-inflammatory agent (see Patent Document 5), an extract of *chlorella* as an aromatase activity accelerator (see Patent Document 6), and one or more plant extracts selected from *Matricaria chamomilla, Clematis apiifolia* var. *biternata*, and *Hedera helix* as a protease activity accelerator (see Patent Document 7).

In addition, no prior art regarding a cell activation agent, a collagen production accelerator, a whitening agent, an antioxidant, an anti-inflammatory agent, an aromatase activity accelerator, a skin external preparation, and food, which contain an extract of *Hibiscus makinoi* as an active ingredient is not recognized.

[Patent Document 1] Japanese Patent Application Laid-Open No. 2001-131045
[Patent Document 2] Japanese Patent Application Laid-Open No. 10-203952
[Patent Document 3] Japanese Patent Application Laid-Open No. 2003-89630
[Patent Document 4] Japanese Patent Application Laid-Open No. 10-182413
[Patent Document 5] Japanese Patent Application Laid-Open No. 6-9391
[Patent Document 6] Japanese Patent Application Laid-Open No. 2004-189609
[Patent Document 7] Japanese Patent Application Laid-Open No. 2003-226613

DISCLOSURE OF THE INVENTION

Problems to be Solved by the Invention

Conventionally used cell activation agents, collagen production accelerators, whitening agents, antioxidants, anti-inflammatory agents, aromatase activity accelerators, protease activity accelerators, skin external preparations, and food may be insufficient as essential effects in some cases, and development of a more excellent active ingredient has been expected. The present invention was made in view of such a conventional problem, and an object thereof is to provide a cell activation agent, a collagen production accelerator, a whitening agent, an antioxidant, an anti-inflammatory agent, an aromatase activity accelerator, a protease activity accelerator, a skin external preparation, and food, which are naturally occurring, have high safety, and are more excellent in effects.

Means for Solving the Problems

The present inventors made studies on various natural products in order to solve the above described problems, and as a result, they found that an extract of *Hibiscus makinoi* is excellent in cell activation action, collagen production acceleration action, whitening action, antioxidation action, anti-inflammatory action, aromatase activity acceleration action, and protease activity acceleration action, which led to completion of the present invention. That is, the present invention provides a cell activation agent, a collagen production accelerator, a whitening agent, an antioxidant, an anti-inflammatory agent, an aromatase activity accelerator, a protease activity accelerator, a skin external preparation, and food, which contain an extract of *Hibiscus makinoi*.

The extract of *Hibiscus makinoi* can be extracted from *Hibiscus makinoi* with at least one selected from the group consisting of water, saline, a phosphate buffer, a polar organic solvent, a supercritical fluid, and a subcritical fluid.

In particular, (1) an extract extracted with an aqueous lower alcohol solution under normal temperature and normal pressure and (2) an extract extracted with water under high temperature and high pressure are preferable. After extracting with an aqueous lower alcohol solution and water, moisture may be removed by performing freeze dry, and the like.

It is preferable to use dry pulverized *Hibiscus makinoi* as the *Hibiscus makinoi* from the viewpoint of being excellent in effects of cell activation, collagen production acceleration, whitening, antioxidation, anti-inflammatory, aromatase activity acceleration, and protease activity acceleration.

It is considered that an extract of *Hibiscus makinoi* functions as a glutathione production accelerator and a tyrosinase activity inhibitor, thereby exerting a whitening effect. It is considered that an extract of *Hibiscus makinoi* functions as a DPPH radical scavenger and an SOD-like active agent (superoxide scavenger), thereby exerting an antioxidation effect. Further, it is considered that an extract of *Hibiscus makinoi* functions as a hyaluronidase activity inhibitor, thereby exerting an anti-inflammatory effect.

Effect of the Invention

According to the present invention, a cell activation agent, a collagen production accelerator, a whitening agent, an antioxidant, an anti-inflammatory agent, an aromatase activity accelerator, and protease activity accelerator, which have excellent effects, can be provided. Further, blending an extract of *Hibiscus makinoi* in a skin external preparation allows to provide an anti-aging improving skin external preparation exerting an excellent effect in prevention and improvement of skin aging symptoms such as wrinkles, sagging, skin tension, spots and somberness, a whitening skin external preparation exerting an excellent effect in melanin production suppression, and an anti-inflammatory skin external preparation an exerting excellent anti-inflammatory effect. Furthermore, by blending an extract of *Hibiscus makinoi* in food, food exerting an excellent effect in beautification, health maintenance, and nutritional support can be provided.

BEST MODES FOR CARRYING OUT THE INVENTION

*Hibiscus makinoi* used in the present invention is a plant of Malvaceae, *Hibiscus*. *Hibiscus makinoi* is grown in the Southwest Islands (Nansei Islands) such as the Ishigaki Island, and the like, and is available in these areas.

An extract of *Hibiscus makinoi* is obtained by extracting a *Hibiscus makinoi* raw material (referred to *Hibiscus makinoi* that is an object to be extracted). For extraction, any tissue of *Hibiscus makinoi* can be employed, but from the viewpoint that extraction becomes easy and efficient, it is recommended to use bark, leaves, or fruits of *Hibiscus makinoi*. *Hibiscus makinoi* may be extracted as a raw, but in considering extraction efficiency, it is preferable to extract after performing treatments such as cutting into small pieces, drying, pulverization, and the like.

As an extraction method, a method of immersing in an extraction solvent or a method of using a supercritical fluid or a subcritical fluid can be applied. In order to increase extraction efficiency, extraction may be preformed while stirring, or while homogenizing a *Hibiscus makinoi* raw material by a homogenizer, a mixer, or the like in an extraction solvent.

As an extraction solvent, solvents such as water; lower alcohols (referred to alcohols having 6 or less carbon atoms) such as methanol, ethanol, propanol, and isopropanol; polyhydric alcohols such as 1,3-butylene glycol, propylene glycol, dipropylene glycol, and glycerin; ethers such as ethyl ether and propyl ether; esters such as butyl acetate and ethyl acetate; ketones such as acetone and ethyl methyl ketone can be used, one kind, or two or more kinds are selected from these solvents to be used. In addition, the above extraction solvents except for water correspond to polar organic solvents.

As the extraction solvent, saline, a phosphate buffer, a phosphate buffered saline, and the like may also be used. Further, one kind, or two or more kinds of supercritical fluids or subcritical fluids such as water, carbon dioxide, ethylene, propylene, ethanol, methanol, and ammonia may be used. That is, supercritical extraction or subcritical extraction of *Hibiscus makinoi* may be performed by using water, carbon dioxide, ethylene, propylene, ethanol, methanol, ammonia, and the like.

As an extraction temperature, it is suitable to set at a temperature from about 5° C. to a boiling point or less of an extraction solvent. An extraction time varies depending on a kind of an extraction solvent or an extraction temperature, but it is suitable to set for about 1 hour to about 14 days.

Further, the extraction can be performed at a normal temperature (room temperature, for example, at 10 to 40° C.) and a normal pressure (1 atm=about 100 kPa), or also may be performed at a high temperature (for example, at 50 to 200° C., preferable at 50 to 150° C.) and a high pressure (for example, more than 100 kPa and 500 kPa or less, preferably more than 100 kPa and 300 kPa or less) using an autoclave, or the like.

When supercritical extraction or subcritical extraction is preformed, it is preferable to carry out extraction at a critical temperature or more and a critical pressure or more of a fluid to be used. For example, it is preferable to perform extraction at 31° C. or more and 7.3 MPa or more when carbon dioxide is used as a supercritical fluid, it is preferable to perform extraction at 239° C. or more and 8.1 MPa or more when methanol is used, and it is preferable to perform extraction at 374° C. or more and 22.1 MPa or more when water is used.

Particularly preferable extraction of *Hibiscus makinoi* is extraction by an aqueous lower alcohol solution (for example, an aqueous methanol solution or an aqueous ethanol solution, in particular, an aqueous ethanol solution) under normal temperature and normal pressure or extraction by water at a high temperature (for example, 50 to 200° C., preferable 50 to 150° C., in particular, 120° C.) and a high pressure. By performing such extraction, an extract excellent in functions as a cell activation agent, a collagen production accelerator, a whitening agent, an antioxidant, an anti-inflammatory agent, an aromatase activity accelerator, or a protease activity accelerator can be effectively and certainly obtained.

Examples of an extract of *Hibiscus makinoi* include (1) an extraction solution of *Hibiscus makinoi*, (2) those obtained by concentrating and/or solidifying with drying an extraction solution of *Hibiscus makinoi*, thereafter dissolving again in water or a polar organic solvent, (3) those subjected to a purification treatment such as decoloration, deodorization, desalting, and the like or a fractional treatment such as chromatography, to such an extent as not to impair the physiological action, and (4) those obtained by freeze-drying an extraction solution of *Hibiscus makinoi* and an extraction solution of *Hibiscus makinoi* subjected to the above treatments to form into a state of being used by dissolving again in water or a polar organic solvent at the time of use.

Herein, the extract of *Hibiscus makinoi* indicates those in a state of dispersing or dissolving a component extracted from a *Hibiscus makinoi* raw material in an extraction solvent. Examples of the above polar organic solvent include lower alcohols, polyhydric alcohols, ethers, esters, and ketones, which are mentioned above.

The extract of *Hibiscus makinoi* has excellent cell activation action, collagen production acceleration action, whitening action, antioxidation action, anti-inflammatory action, aromatase activity acceleration action, and protease activity acceleration action, and can be used as a cell activation agent, a collagen production accelerator, a whitening agent, an antioxidant, an anti-inflammatory agent, an aromatase activity accelerator, a protease activity accelerator, a skin external preparation, and food.

A cell activation agent containing an extract of *Hibiscus makinoi* as an active ingredient has cell activation action for various cells, and exerts an excellent cell activation effect particularly for a dermal fibroblast. A content of the extract of *Hibiscus makinoi* in the cell activation agent is preferably 0.0001 to 100% by mass, and more preferably 0.001 to 50% by mass on the basis of the total amount of the cell activation agent.

A collagen production accelerator containing an extract of *Hibiscus makinoi* as an active ingredient has collagen production acceleration action, and exerts an excellent collagen production acceleration effect particularly for collagen I production in a dermal fibroblast and collagen IV production in an epidermal keratinocyte. A content of the extract of *Hibiscus makinoi* in the collagen production accelerator is preferably 0.0001 to 100% by mass, and more preferably 0.001 to 50% by mass on the basis of the total amount of the collagen production accelerator.

A whitening agent containing an extract of *Hibiscus makinoi* as an active ingredient has whitening action, and particularly exerts an excellent effect for improving pigmentation symptoms such as pigmented spots and freckles by a whitening effect based on glutathione production acceleration action, tyrosinase activity suppression action, and melanin production inhibition action. A content of the extract of *Hibiscus makinoi* in the whitening agent is preferably 0.0001 to 100% by mass, and more preferably 0.001 to 50% by mass on the basis of the total amount of the whitening agent.

An antioxidant containing an extract of *Hibiscus makinoi* as an active ingredient has antioxidation action, and particularly exerts an excellent effect by antioxidation action based on DPPH radical scavenging action and SOD-like activity action (superoxide scavenging action). A content of the extract of *Hibiscus makinoi* in the antioxidant is preferably 0.0001 to 100% by mass, and more preferably 0.001 to 50% by mass on the basis of the total amount of the antioxidant.

An anti-inflammatory agent containing an extract of *Hibiscus makinoi* as an active ingredient has anti-inflammatory action, and particularly exerts an excellent effect by anti-inflammatory action based on hyaluronidase activity inhibition action. A content of the extract of *Hibiscus makinoi* in the anti-inflammatory agent is preferably 0.0001 to 100% by mass, and more preferably 0.001 to 50% by mass on the basis of the total amount of the anti-inflammatory agent.

An aromatase activity accelerator containing an extract of *Hibiscus makinoi* as an active ingredient exerts an excellent beautiful skin effect and an excellent anti-aging effect by estrogen production acceleration action based on aromatase activity acceleration action. A content of the extract of *Hibiscus makinoi* in the aromatase activity accelerator is preferably 0.0001 to 100% by mass, and more preferably 0.001 to 50% by mass on the basis of the total amount of the aromatase activity accelerator.

A protease activity accelerator containing an extract of *Hibiscus makinoi* as an active ingredient promotes self-peeling that is turnover of its own skin by activating protease inside the skin and exerts an excellent beautiful skin effect and an excellent anti-aging effect. A content of the extract of *Hibiscus makinoi* in the protease activity accelerator is preferably 0.0001 to 100% by mass, and more preferably 0.001 to 50% by mass on the basis of the total amount of the protease activity accelerator.

Further, by blending the extract of *Hibiscus makinoi* in a skin external preparation, an anti-aging improving skin external preparation exerting excellent effects of prevention and improvement of skin aging symptoms, and a whitening skin external preparation exerting an excellent effect for melanin production inhibition, and an anti-inflammatory skin external preparation exerting an excellent effect for anti-inflammatory property can be obtained. A content of the extract of *Hibiscus makinoi* when blended in the skin external preparation can be adjusted according to a kind of skin external preparation, application purposes, or the like, but from the viewpoints of effects, safety, etc., it is preferably 0.0001 to 50.0% by mass, and more preferably 0.001 to 10.0% by mass on the basis of the total amount of the skin external preparation.

Formulations of skin external preparations blending an extract of *Hibiscus makinoi* (skin external preparations applicable as a cell activation agent, a collagen production accelerator, a whitening agent, an antioxidant, an anti-inflammatory agent, an aromatase activity accelerator, a protease activity accelerator, and the like) are optional, and the skin external preparations can be provided as, for example, soluble form such as a lotion, emulsion form such as a cream and an emulsion, and dispersion form such as a calamine lotion. Further, the skin external preparations can be also provided in various formulations such as aerosol filled with a spraying agent, an ointment agent, a powder, and a granule.

The skin external preparations blending an extract of *Hibiscus makinoi* can suitably contain, in addition to the extract of *Hibiscus makinoi*, an oily component, a moisturizing agent, a powder, a pigment, an emulsifier, a solubilizer, a washing agent, an ultraviolet ray absorber, a thickener, a medical agent, a fragrance, a resin, a fungicide, alcohols, and the like, which are generally blended in medical products, medicated cosmetics, skin cosmetics, hair cosmetics, and washing agents, according to necessity. Further, within the range where the effects of the present invention are not damaged, the skin external preparation can be also used in combination with other cell activation agent, collagen production accelerator, whitening agent, antioxidant, anti-inflammatory agent, aromatase activity accelerator, or protease activity accelerator.

Furthermore, an extract of *Hibiscus makinoi* can be also used as food, beverage and medical products for the purposes of beautification, health maintenance, and nutritional support. The food, beverage and medical products blending an extract of *Hibiscus makinoi* have optional formulations, and can be provided as general formulations such as a liquid agent (e.g., a drinking agent and drops), a solid agent (e.g., gum and candy), or a capsule, a powder, a granule, a tablet, and the like.

The food, beverage and medical products blending an extract of *Hibiscus makinoi* can suitably contain, in addition to the extract of *Hibiscus makinoi*, saccharides, salts, alcohols, amino acid, a colorant, a fragrance, a sweetener, an acidulant, an antiseptic agent, a thickener, a chemical agent, and the like, which are generally blended in food, beverage, medical products, medicated cosmetics, according to the necessity. Further, within the range where the effects of the present invention are not damaged, the food, beverage and medical products can be also used in combination with other cell activation agent, collagen production accelerator, whitening agent, antioxidant, anti-inflammatory agent, aromatase activity accelerator, or protease activity accelerator.

EXAMPLES

Hereinafter, production examples of an extract of *Hibiscus makinoi* and experiments for evaluation of each action will be more specifically described, however, the present invention is not limited thereto.

Production Example 1

To a dry pulverized matter of bark or leaves of *Hibiscus makinoi*, 20-hold amount of ethanol (50% by mass) was added at room temperature and extracted for 2 hours while stirring, and then, an insoluble substance was removed by filtration. After concentration under reduced pressure, the residue was freeze-dried to obtain an extract of *Hibiscus makinoi*.

Production Example 2

To a dry pulverized matter of bark, leaves, or fruits of *Hibiscus makinoi*, 20-hold amount of purified water was added, and extracted by heating at 120° C. for 20 minutes using an autoclave. An insoluble substance was removed by suction filtration while keeping a high temperature, then the residue was freeze-dried to obtain an extract of *Hibiscus makinoi*.

Experiments for evaluation of each action were carried out using the extracts of *Hibiscus makinoi* obtained in the above Production Examples.

Example 1

Evaluation Experiment of Cell Activation Action for Dermal Fibroblast

In this evaluation experiment, the extract of bark of *Hibiscus makinoi* obtained by the production method described in Production Example 1 was used as a sample. The evaluation was carried out according to the following procedure. Normal human dermal fibroblasts were seeded in a 96 well microplate so as to be $2.0 \times 10^4$ cells per 1 well. For a seeding medium, a Dulbecco's modified eagle medium (DMEM) to which 1% by mass of a fetal bovine serum (FBS) was added was used. After culturing for 24 hours, the medium was replaced with a sample culture solution adjusted to each sample concentration in the DMEM medium added with 1% by mass of FBS, and further cultured for 48 hours.

Then, the medium was replaced with a medium containing 400 μg/ml of 3-(4,5-dimethyl-2-thiazolyl)-2,5-diphenyltetrazolium bromide (MTT) and cultured for 2 hours, and formazan generated by ring opening of a tetrazolium ring was extracted with 2-propanol. An absorbance at 550 nm was measured by a microplate reader, and at the same time, an absorbance at 650 nm was measured as a turbidity, and cell activation action was evaluated using a gap between the both measured values.

Cell activation action for a dermal fibroblast was evaluated as a relative value when cell activation action in a control without adding a sample was assumed to be 100. Table 1 shows the evaluation results thereof. In addition, ** in the table represents less than 1% (P<0.01) of a significance probability in a t-test.

TABLE 1

| Sample concentration (mg/mL) | % of control | t-test |
|---|---|---|
| control | 100 | — |
| 0.13 | 110 | ** |
| 0.25 | 121 | ** |

**: P < 0.01

As apparent from Table 1, significant dermal fibroblast activation action was recognized in a medium to which an extract of *Hibiscus makinoi* was added. In particular, when the sample was added in an amount of 0.13 to 0.25 mg/mL, as compared with a control, significant dermal fibroblast activation action was recognized at less than 1% of a risk ratio. According to these facts, it was revealed that an extract of *Hibiscus makinoi* has excellent dermal fibroblast activation action.

Example 2

Evaluation Experiment of I Type Collagen Production Acceleration Action for Dermal Fibroblast In this evaluation experiment, the extract of bark of *Hibiscus makinoi* obtained by the production method described in Production Example 1 was used as a sample. The evaluation was carried out according to the following procedure. Normal human dermal fibroblasts were seeded in a 96 well microplate so as to be $2.0 \times 10^4$ cells per 1 well. For a seeding medium, a Dulbecco's modified eagle medium (DMEM) to which 5% by mass of a fetal bovine serum (FBS) was added was used. After culturing for 24 hours, the medium was replaced with a sample culture solution adjusted to each sample concentration in the DMEM medium added with 0.5% by mass of FBS, and further cultured for 24 hours.

An amount of I type collagen secreted in the medium supernatant was measured by using the enzyme-linked immunosorbent assay (ELISA). First, the I type collagen secreted in the medium supernatant was reacted with a rabbit anti-human I type collagen polyclonal antibody (CHEMICON), and then labeled by using a peroxidase labeled antirabbit IgG polyclonal antibody (HISTOFINE; Nichirei Corporation) as a secondary antibody. Then, 2,2'-azinobis(3-ethylbenzothiazoline-6-sulfonate) diammonium salt (ABTS) and hydrogen peroxide were added to the labeled peroxidase to be reacted, thereafter measuring an absorbance at 405 nm by a microplate reader.

Further, a protein amount of each well was measured by a BCA Protein Reagent Assay kit made by PIERCE Corporation, and a production amount of I type collagen per a unit protein amount was found.

The I type collagen production acceleration action for a dermal fibroblast was evaluated as a relative value when a production amount of I type collagen per a unit protein amount in a control without adding a sample was assumed to be 100. Table 2 shows the evaluation results thereof. In addition, in the table, less than 5% (P<0.05) of a significance probability represents * and less than 1% (P<0.01) of a significance probability represents ** in a t-test.

TABLE 2

| Sample concentration (mg/mL) | % of control | t-test |
|---|---|---|
| control | 100 | — |
| 0.13 | 309 | * |
| 0.25 | 348 | ** |

**: P < 0.01,
*: 0.01 < P < 0.05

As apparent from Table 2, significant I type collagen production acceleration action for a dermal fibroblast was recognized in a medium to which an extract of *Hibiscus makinoi* was added. In particular, when the sample was added in an amount of 0.25 mg/mL, as compared with a control, significant I type collagen production acceleration action was recognized at less than 1% of a risk ratio. According to these facts, it was revealed that an extract of *Hibiscus makinoi* has excellent I type collagen production acceleration action.

Example 3

Evaluation Experiment of IV Type Collagen Production Acceleration Action for Epidermal Keratinocyte In this evaluation experiment, the extract of leaves of *Hibiscus makinoi* obtained by the production method described in Production Example 1 was used as a sample. The evaluation was carried out according to the following procedure. Human epidermal para-keratinocyte were seeded in a 96 well microplate so as to be $2.0 \times 10^4$ cells per 1 well. For a seeding medium, a Dulbecco's modified eagle medium (DMEM) to which 5% by mass of a fetal bovine serum (FBS) was added was used. After culturing for 24 hours, the medium was replaced with a sample culture solution adjusted to each sample concentration in the DMEM medium added with 5% by mass of FBS, and further cultured for 5 days.

An amount of IV type collagen secreted in the medium supernatant was measured by using the sandwich ELISA method. First, the IV type collagen secreted in the medium supernatant was reacted with a monoclonal antibody (recognition site: α2 chain) to the IV type collagen, and then reacted with a biotinylated polyclonal antibody.

Then, an avidinated horseradish peroxidase was added to be bound to a biotin portion of the biotinylated polyclonal antibody. 3,3',5,5'-tetramethylbenzidine that is a substrate of peroxidase was added to develop color, and an absorbance at 650 nm was measured by a microplate reader.

Further, a protein amount of each well was measured by a BCA Protein Reagent Assay kit made by PIERCE Corporation, and a production amount of IV type collagen per a unit protein amount was found.

IV type collagen production acceleration action for epidermal keratinocyte was evaluated as a relative value when a production amount of IV type collagen per a unit protein amount in a control without adding a sample was assumed to be 100. Table 3 shows the evaluation results thereof. In addition, ** in the table represents less than 1% ($P<0.01$) of a significance probability in a t-test.

TABLE 3

| Sample concentration (mg/mL) | % of control | t-test |
|---|---|---|
| control | 100 | — |
| 0.5 | 761 | ** |
| 1.0 | 1871 | ** |

**: $P < 0.01$

As apparent from Table 3, significant IV type collagen production acceleration action for epidermal para-keratinocyte was recognized in a medium to which an extract of *Hibiscus makinoi* was added. In particular, when the sample was added in an amount of 0.5 to 1.0 mg/mL, as compared with a control, significant IV type collagen production acceleration action was recognized at less than 1% of a risk ratio. According to these facts, it was revealed that the extract of *Hibiscus makinoi* has excellent IV type collagen production acceleration action.

Example 4

Evaluation Experiment of Melanin Production Suppression Action for B16 Mouse Melanoma Cell In this evaluation experiment, the extract of bark of *Hibiscus makinoi* obtained by the production method described in Production Example 1 was used as a sample. The evaluation was carried out according to the following procedure. B16 mouse melanoma (B16F0) cells were seeded in a 90 mm-dish so as to be 18,000 cells per one dish. For a seeding medium, a Dulbecco's modified eagle medium (DMEM) to which 5% by mass of a fetal bovine serum (FBS) was added was used. After culturing for 24 hours, the medium was replaced with a sample culture solution adjusted to each sample concentration in the DMEM medium added with 5% by mass of FBS, and further cultured for 5 days.

In this experiment, a DMEM medium added with 5% by mass of FBS without adding a sample was used as a negative control, and a DMEM medium added with 5% by mass of FBS containing sodium lactate with a concentration of 50 mM was used as a positive control.

After completion of the culture, cells were recovered by a trypsin treatment using 0.25% of trypsin, and transferred into a 1.5 mL-microtube and centrifugally operated to obtain a cell precipitate. A state of color of the obtained precipitate was determined by visual observation. The criteria of the visual determination were shown in Table 4. In addition, the negative control was evaluated to be 5, and the positive control was evaluated to be 1 as the criteria of the visual determination.

Further, a tissue dissolving agent (product name: Solvable) was added to the precipitate obtained above and boiled, and then cooled to room temperature, and an absorbance at 500 nm was measured by a spectrophotometer (spectrophotometer U-3010, manufactured by HITACHI, Ltd.). Melanin production suppression action for a B16 mouse melanoma cell was evaluated by the above determination and an absorbance at 500 nm. Table 5 shows the evaluation results thereof.

TABLE 4

| Evaluation score | Criteria |
|---|---|
| 1 | In the same level as the positive control (nearly white) |
| 2 | Slightly blackened as compared with the positive control (light brown) |
| 3 | In the middle between the positive control and the negative control (brown) |
| 4 | Blackening is somewhat suppressed as compared with the negative control (black brown) |
| 5 | In the same level as the negative control (nearly black) |

TABLE 5

| Sample concentration (μg/mL) | Absorbance Abs. (500 nm) | Visual determination |
|---|---|---|
| Negative control | 0.280 | 5 |
| Positive control | 0.023 | 1 |
| 1 | 0.185 | 3 |
| 100 | 0.071 | 2 |

As apparent from Table 5, when the medium added with 100 μg/mL of a sample was used, slight blackening was only recognized as compared with the positive control. According to the fact, it was revealed that an extract of *Hibiscus makinoi* has excellent melanin production suppression action and whitening action based thereon.

Example 5

Evaluation Experiment of Glutathione Production Acceleration Action for Epidermal Melanin Cell In this evaluation experiment, the extract of bark of *Hibiscus makinoi* obtained by the production method described in Production Example 1 was used as a sample. The evaluation was carried out according to the following procedure. Normal human epidermal melanin cells were seeded in a collagen-coated 96 well microplate so as to be $3.0 \times 10^4$ cells per 1 well. For a seeding medium, a MGM medium supplemented with 2% FCS, a fibrocyte growth factor (hereinafter, FGF) (3 ng/mL), insulin (5 μg/mL) and hydrocortisone (0.18 μg/mL) was used. The medium was cultured at 37° C. for 24 hours under 5% $CO_2$, then 100 μL of a medium adjusted to each sample concentration was added, and cultured for 48 hours.

After the culture, the medium was washed with a phosphate buffered saline (hereinafter, PBS) (pH 7.5) containing phenylmethylsulfonyl floride ((PMSF) 0.1 mM), and 100 mL of PBS containing PMSF (0.1 mM) was added and performed an ultrasonic disintegration treatment for 5 seconds, thereafter transferring the treated solution to another plate.

Then, to the treated solution, 25 µL an aqueous 5% sodium hydrogen carbonate solution containing 2 mM of NADPH was added, and further, thereto was added 125 µL of a phosphate buffer containing 0.5 mM of ethylenediamine tetraacetate to which 25 µL of a 0.1 M phosphate buffer containing ethylenediamine tetraacetate (0.5 mM), BSA (1 mg/mL) and glutathione reductase (12.5/mL) was added. After allowing to stand at 37° C. for 10 minutes, 25 µL of a 0.1 M phosphate buffer containing 0.5 mM of ethylenediamine tetraacetate and 10 mM of 5,5'-dithiobis(2-nitrobenzoate) was added to each well, and a glutathione concentration was measured from an absorbance at 450 nm.

Further, a protein amount was measured by a BCA Protein Reagent Assay kit made by PIERCE Corporation, and a production amount of glutathione per a unit protein amount was found.

Glutathione production acceleration action for an epidermal melanin cell was evaluated as a relative value when a production amount of glutathione per a unit protein amount in a control without adding a sample was assumed to be 100. Table 6 shows the evaluation results thereof. In addition, ** in the table represents less than 1% (P<0.01) of a significance probability in a t-test.

TABLE 6

| Sample concentration (mg/mL) | % of control | t-test |
|---|---|---|
| control | 100 | — |
| 0.25 | 123.5 | ** |
| 1.00 | 136.1 | ** |

**: P < 0.01

As apparent from Table 6, significant glutathione production acceleration action was recognized in a medium to which an extract of *Hibiscus makinoi* was added. In particular, when the sample was added in an amount of 0.25 to 1.0 mg/mL, as compared with the control, significant glutathione production acceleration action was recognized at less than 1% of a risk ratio. According to these facts, it was revealed that an extract of *Hibiscus makinoi* has excellent glutathione production acceleration action and whitening action based thereon.

Example 6

Evaluation Experiment of Tyrosinase Activity Inhibition Action for Epidermal Melanin Cell In this evaluation experiment, the extract of bark of *Hibiscus makinoi* obtained by the production method described in Production Example 2 was used as a sample. The evaluation was carried out according to the following procedure. Normal human epidermal melanin cells were seeded in a 96 well microplate so as to be $3.0 \times 10^4$ cells per 1 well. For a seeding medium, Medium 154S made by Kurabo Industries, Ltd. was used. After culturing for 24 hours, the medium was replaced with a sample culture solution adjusted to each sample concentration in Medium 154S, and further cultured for 48 hours.

Then, the culture solution was replaced with 75 µL of a 1% by mass of Triton-X-containing phosphate buffer, and the cells were completely dissolved. 50 µL of the solution was used as a crude enzyme solution, thereto was added 50 µL of a phosphate buffer containing 0.05% by mass of L-Dopa that is a substrate, and allowed to stand still at 37° C. for 2 hours.

Absorbances at 405 nm were measured immediately after adding the substrate and at completion of the reaction by a microplate reader, and a value found by introducing a gap between the both measured values in the following formula was defined to be a Dopa melanin production amount.

{(Value at 405 nm after reaction−value at 405 nm before reaction)−2.166}/5.238

Further, a protein amount was measured by a BCA Protein Reagent Assay kit made by PIERCE Corporation, and a Dopa melanin production amount per a unit protein amount was found.

Tyrosinase activity inhibition action for an epidermal melanin cell was evaluated as a relative value when a Dopa melanin production amount per a unit protein amount in a control without adding a sample was assumed to be 100. Table 7 shows the evaluation results thereof. In addition, ** in the table represents less than 1% (P<0.01) of a significance probability in a t-test.

TABLE 7

| Sample concentration (mg/mL) | % of control | t-test |
|---|---|---|
| control | 100 | — |
| 0.25 | 76.5 | ** |
| 1.00 | 56.4 | ** |

**: P < 0.01

As apparent from Table 7, significant tyrosinase activity inhibition action was recognized in a medium to which an extract of *Hibiscus makinoi* was added. In particular, when the sample was added in an amount of 0.25 to 1.0 mg/mL, as compared with the control, significant tyrosinase activity inhibition action was recognized at less than 1% of a risk ratio. According to these facts, it was revealed that an extract of *Hibiscus makinoi* has excellent tyrosinase activity inhibition action and whitening action based thereon.

Example 7

Evaluation Experiment of DPPH Radical Scavenging Action

In this evaluation experiment, the extract of leaves of *Hibiscus makinoi* obtained by the production method described in Production Example 2 was used as a sample. The evaluation was carried out according to the following procedure. A sample solution adjusted at each sample concentration by 50% by mass of ethanol in an each amount of 100 µL was added to a 96 well microplate. Thereto was further added 0.2 mM of a 1,1-diphenyl-2-picrylhydrazyl (DPPH) ethanol solution in an each amount of 100 µL.

After sufficiently mixing, the solution was stood still in a dark room at room temperature for 24 hours, and then an absorbance at 516 nm derived from a DPPH radical was measured. When an absorbance in the case of not adding a sample was (A) and an absorbance in the case of adding a sample was (B), a value found by the following formula was defined to be a DPPH radical elimination ratio. The DPPH radical scavenging action was evaluated by the DPPH radical elimination ratio. Table 8 shows the evaluation results thereof.

{1−(B)/(A)}×100 (%)

TABLE 8

| Sample concentration (mg/mL) | DPPH radical elimination ratio (%) |
|---|---|
| 1.0 | 87.7 |
| 10 | 96.6 |

As apparent from Table 8, it was revealed that an extract of *Hibiscus makinoi* has antioxidant action based on the DPPH radical scavenging action.

Example 8

Evaluation Experiment of SOD-like Activity Action

In this evaluation experiment, the extract of leaves of *Hibiscus makinoi* obtained by the production method described in Production Example 2 was used as a sample. The evaluation was carried out according to the following procedure. To 75 mL of a HANK'S (+) solution containing 0.25 mM of WST-1 and 1 mM of hypoxanthine, 25 mL of a sample solution adjusted to each sample concentration in a HANK'S (+) solution was added. Further, thereto was added 25 mL (0.0075 units) of xanthine oxidase, and reacted at 37° C. for 15 minutes, and then an absorbance at 450 nm was measured.

When an absorbance in the case of only adding a HANK'S (+) solution in place of a sample solution was (A) and an absorbance in the case of adding a sample solution was (B), a value found by the following formula was defined to be a superoxide anion elimination ratio. The SOD-like activity action was evaluated by the superoxide anion elimination ratio. Table 9 shows the evaluation results thereof.

$$\{1-(B)/(A)\}\times 100\ (\%)$$

TABLE 9

| Sample concentration (μg/mL) | Superoxide anion elimination ratio (%) |
|---|---|
| 50.0 | 57.5 |
| 200 | 87.2 |

As apparent from Table 9, it was revealed that an extract of *Hibiscus makinoi* has antioxidant action based on the SOD-like activity action.

Example 9

Evaluation Experiment of Hyaluronidase Activity Inhibition Action

In this evaluation experiment, the extract of leaves of *Hibiscus makinoi* obtained by the production method described in Production Example 2 was used as a sample. The evaluation was carried out according to the following procedure. A commercially available potassium hyaluronate salt (derived from human umbilical cord) was dissolved in a 0.1 M phosphate buffer solution (pH 7.0) so as to be 0.9 mg/mL to prepare a substrate solution. A commercially available hyaluronidase (derived from bovine testis) was dissolved in a 0.1 M phosphate buffer solution (pH 7.0) so as to be 5300 unit/mL to prepare an enzyme solution. In addition, the enzyme solution was prepared immediately before use.

A test tube was charged with 0.1 mL of the sample solution adjusted at each sample concentration and 0.03 mL of the enzyme solution in a 0.1 M phosphate buffer solution (pH 7.0), and reacted at 37° C. for 20 minutes. Then, 0.06 mL of an activating agent was added thereto and reacted at 37° C. for 20 minutes. Thereto was further added 0.15 mL of a substrate solution, and reacted at 37° C. for 1 hour. Thereto was added 0.06 mL of 0.4N NaOH, and immediately after terminating the reaction, the mixture was cooled with ice, and 0.06 mL of a boric acid buffer solution (pH 9.1) was added, and the mixture was boiled for 3 minutes, and then further cooled with ice.

A p-DABA solution (Ehrlich reagent) in an amount of 2.0 mL was added, and reacted at 37° C. for 20 minutes, and then the solution was transferred from the each test tube to a 96 well microplate, and an absorbance at 585 nm was measured using a microplate reader. When activity of hyaluronidase is inhibited, N-acetylglucosamine (GlcNAc) that is a decomposed product of hyaluronic acid decreases, and an absorbance by a Morgan-Elson reaction is lowered.

When an absorbance in the case of using a 0.1 M phosphate buffer solution without adding a sample was a control absorbance, and an absorbance in the case of using a sample solution was a sample absorbance, a value found by the following formula was defined to be a hyaluronidase activity inhibition ratio. The hyaluronidase activity inhibition action was evaluated by the hyaluronidase activity inhibition ratio. Table 10 shows the evaluation results thereof. In addition, in the table, less than 5% (P<0.05) of a significance probability represents * and less than 1% (P<0.01) of a significance probability represents ** in a t-test.

(Control absorbance−sample absorbance)/control absorbance×100 (%)

TABLE 10

| Sample concentration (mg/mL) | Hyaluronidase activity inhibition ratio (%) | t-test |
|---|---|---|
| 5.0 | 16.6 | * |
| 10 | 21.7 | ** |

**: P < 0.01,
*: 0.01 < P < 0.05

As apparent from Table 10, significant hyaluronidase activity inhibition action was recognized in an extract of *Hibiscus makinoi*. In particular, when the sample solution with a sample concentration of 5.0 mg/mL was used, as compared with the control, significant hyaluronidase activity inhibition action was recognized at less than 1% of a risk ratio. According to these facts, it was revealed that an extract of *Hibiscus makinoi* has excellent hyaluronidase activity inhibition action and anti-inflammatory action based thereon.

Example 10

Evaluation Experiment of Aromatase Activity Acceleration Action

In this evaluation experiment, the extract of leaves of *Hibiscus makinoi* obtained by the production method described in Production Example 1 was used as a sample. The evaluation was carried out according to the following procedure. To 4 μL of a sample solution adjusted to each sample concentration, 96 μL of a mixed solution containing NADP$^+$, MgCl$_2$, glucose-6-phosphoric acid, glucose-6-phosphoric dehydrogenase, and insect cell membrane protein (control) was added to prepare a reaction solution. Subsequently, the reaction solution was heated at 37° C. for 10 minutes.

Then, to the reaction solution, 100 μL of a solution containing 15 nM of CYP19 (aromatase) and 50 μM of 7-methoxy-4-trifluoromethylcoumarin (substrate) was added. Subsequently, the reaction solution was heated at 37° C. for 30 minutes, then 75 μL of a 100 μM tris base was added thereto, and the reaction was quenched.

According to this reaction, aromatase decomposes 7-methoxy-4-trifluoromethylcoumarin that is a substrate, and 7-hydroxy-4-trifluoromethylcoumarin that is a fluorescent substance was produced. Herein, a fluorescence measurement was carried out at an excitation wavelength of 409 nm and a fluorescence wavelength of 530 nm.

Aromatase activity acceleration action was evaluated as a relative value when a value of the fluorescence measurement in the control without adding a sample was assumed to be 100. Table 11 shows the evaluation results thereof. In addition, in the table, less than 5% (P<0.05) of a significance probability represents * and less than 1% (P<0.01) of a significance probability represents ** in a t-test.

TABLE 11

| Sample concentration (mg/mL) | % of control | t-test |
|---|---|---|
| control | 100 | — |
| 0.13 | 168 | * |
| 0.25 | 174 | ** |

**: P < 0.01,
*: 0.01 < P < 0.05

As apparent from Table 11, significant aromatase activity acceleration action was recognized in an extract of *Hibiscus makinoi*. In particular, when the sample solution with a sample concentration of 0.13 mg/mL was used, as compared with the control, significant aromatase activity acceleration action was recognized at less than 1% of a risk ratio. According to these facts, it was revealed that an extract of *Hibiscus makinoi* has excellent aromatase activity acceleration action.

Example 11

Evaluation Experiment of Protease Activity Acceleration Action

In this evaluation experiment, the extract of bark of *Hibiscus makinoi* obtained by the production method described in Production Example 1 was used as a sample. The evaluation was carried out according to the following procedure. To a sample solution adjusted to each sample concentration, trypsinogen was added so as to be 83 mg/mL. Thereto was added fluorescein-modified casein so as to be 0.25% by mass and the reaction solution was prepared. Subsequently, the reaction solution was heated at 37° C. for 24 hours. According to this reaction, trypsinogen was activated to be trypsin, and fluorescein-modified casein serving as a substrate was decomposed by the trypsin. Then, trichloroacetic acid was added to the reaction solution so as to be 3.3% by mass, and the reaction solution was heated at 37° C. for 20 minutes. Thereby, unreacted fluorescein-modified casein was precipitated.

In order to measure fluorescence generated by decomposition of fluorescein-modified casein, a fluorescence measurement was carried out on a supernatant at an excitation wavelength of 485 nm and a fluorescence wavelength of 538 nm. Protease activity acceleration action was evaluated as a relative value when a value of the fluorescence measurement in the control without adding a sample was assumed to be 100. Table 12 shows the evaluation results thereof.

TABLE 12

| Sample concentration (mg/mL) | % of control |
|---|---|
| control | 100 |
| 0.5 | 112 |

According to Table 12, it was revealed that an extract of *Hibiscus makinoi* has protease activity acceleration action.

Then, formula examples of skin external preparations (skin external preparations applicable as a cell activation agent, a collagen production accelerator, a whitening agent, an antioxidant, an anti-inflammatory agent, an aromatase activity accelerator, a protease activity accelerator, etc.) and beverage, which contain an extract of *Hibiscus makinoi*, according to the present invention will be shown. In addition, an amount of each component means % by mass, as otherwise particularly specified.

Prescription Example 1

Emulsion

TABLE 13

| | Components | Amount (mass %) |
|---|---|---|
| (1) | Squalan | 10.0 |
| (2) | Methylphenylpolysiloxane | 4.0 |
| (3) | Hydrogenated palm kernel oil | 0.5 |
| (4) | Hydrogenated soybean phospholipid | 0.1 |
| (5) | Polyoxyethylene sorbitan (20E.O.) monostearate | 1.3 |
| (6) | Sorbitan monostearate | 1.0 |
| (7) | Glycerin | 4.0 |
| (8) | Methyl paraoxybenzoate | 0.1 |
| (9) | Carboxyvinyl polymer | 0.2 |
| (10) | Purified water | 53.9 |
| (11) | Arginine (1 mass % aqueous solution) | 20.0 |
| (12) | Extract of *Hibiscus makinoi* (Production Example 1) | 5.0 |

Production method: Oil phase components of (1) to (6) are dissolved by heating at 80° C. On the other hand, aqueous phase components of (7) to (10) are dissolved by heating at 80° C. Thereto are added the oil phase components while stirring, and uniformly emulsified by a homogenizer. After completion of the emulsification, cooling is initiated, and (11) and (12) are sequentially added and uniformly mixed.

Prescription Example 2

Skin Lotion

TABLE 14

| | Components | Amount (mass %) |
|---|---|---|
| (1) | Ethanol | 15.0 |
| (2) | Polyoxyethylene (40E.O.) hydrogenated castor oil | 0.3 |
| (3) | Fragrance | 0.1 |
| (4) | Purified water | 78.4 |
| (5) | Citric acid | 0.0 |
| (6) | Sodium citrate | 0.1 |
| (7) | Glycerin | 1.0 |
| (8) | Hydroxyethyl cellulose | 0.1 |
| (9) | Extract of *Hibiscus makinoi* (Production Example 2) | 5.0 |

Production method: (2) and (3) are dissolved in (1). After dissolution, (4) to (8) are sequentially added and then sufficiently stirred, and (9) is added and uniformly mixed.

Prescription Example 3

Cream

TABLE 15

| | Components | Amount (mass %) |
|---|---|---|
| (1) | Squalan | 10.0 |
| (2) | Stearic acid | 2.0 |
| (3) | Hydrogenated palm kernel oil | 0.5 |
| (4) | Hydrogenated soybean phospholipid | 0.1 |
| (5) | Cetanol | 3.6 |
| (6) | Lipophilic type glycerin monostearate | 2.0 |
| (7) | Glycerin | 10.0 |
| (8) | Methyl paraoxybenzoate | 0.1 |
| (9) | Arginine (20 mass % aqueous solution) | 15.0 |
| (10) | Purified water | 40.7 |
| (11) | Carboxyvinyl polymer (1 mass % aqueous solution) | 15.0 |
| (12) | Extract of *Hibiscus makinoi* (Production Example 1) | 1.0 |

Production method: oil phase components of (1) to (6) are dissolved by heating at 80° C. On the other hand, aqueous phase components of (7) to (10) are dissolved by heating at 80° C. Thereto are added the oil phase components while stirring, and uniformly emulsified by a homogenizer. After completion of the emulsification, (11) is added, cooling is initiated, and (12) is added at 40° C. and uniformly mixed.

Prescription Example 4

Serum

TABLE 16

| | Components | Amount (mass %) |
|---|---|---|
| (1) | Purified water | 27.5 |
| (2) | Glycerin | 10.0 |
| (3) | Sucrose fatty acid ester | 1.3 |
| (4) | Carboxyvinyl polymer (1 mass % aqueous solution) | 17.5 |
| (5) | Sodium arginate (1 mass % aqueous solution) | 15.0 |
| (6) | Polyglyceryl monolaurate | 1.0 |
| (7) | *Macadamia* nut oil fatty acid phytosteryl | 3.0 |
| (8) | Di(phytosteryl-2-octyldodecyl) N-lauroyl-L-glutamate | 2.0 |
| (9) | Hardened palm oil | 2.0 |
| (10) | Squalan (derived from olive) | 1.0 |
| (11) | Behenyl alcohol | 0.8 |
| (12) | Bee wax | 1.0 |
| (13) | Jojoba oil | 1.0 |
| (14) | 1,3-butylene glycol | 10.0 |
| (15) | L-arginine (10 mass % aqueous solution) | 2.0 |
| (16) | Extract of *Hibiscus makinoi* (Production Example 2) | 5.0 |

Production method: aqueous phase components of (1) to (6) are mixed and dissolved by heating at 75° C. On the other hand, oil phase components of (7) to (14) are mixed and dissolved by heating at 75° C. The oil phase components are then added to the above aqueous phase components to be preliminarily emulsified, and then uniformly emulsified by a homomixer. After completion of the emulsification, cooling is initiated, and (15) is added at 50° C. The mixture is further cooled to 40° C., and (16) is added and uniformly mixed.

Prescription Example 5

Aqueous Gel

TABLE 17

| | Components | Amount (mass %) |
|---|---|---|
| (1) | Carboxyvinyl polymer | 0.5 |
| (2) | Purified water | 86.7 |
| (3) | Sodium hydroxide (10 mass % aqueous solution) | 0.5 |
| (4) | Ethanol | 10.0 |
| (5) | Methyl paraoxybenzoate | 0.1 |
| (6) | Fragrance | 0.1 |
| (7) | Extract of *Hibiscus makinoi* (Production Example 2) | 2.0 |
| (8) | Polyoxyethylene (60E.O.) hydrogenated castor oil | 0.1 |

Production method: (1) is added to (2), and uniformly stirred, and then (3) is added thereto. After uniformly stirring, thereto is added (5) that is dissolved in (4) in advance. After uniformly stirring, (6) to (8) that are mixed in advance are added and uniformly mixed by stirring.

Prescription Example 6

Cleansing Agent

TABLE 18

| | Components | Amount (mass %) |
|---|---|---|
| (1) | Squalan | 81.0 |
| (2) | Polyoxyethylene glyceryl isostearate | 15.0 |
| (3) | Purified water | 3.0 |
| (4) | Extract of *Hibiscus makinoi* (Production Example 1) | 1.0 |

Production method: (1) and (2) are uniformly dissolved. Thereto are sequentially added (3) and (4), and uniformly mixed.

Prescription Example 7

Facial Wash

TABLE 19

| | Components | Amount (mass %) |
|---|---|---|
| (1) | Stearic acid | 16.0 |
| (2) | Myristic acid | 16.0 |
| (3) | Lipophilic type glycerin monostearate | 2.0 |
| (4) | Glycerin | 20.0 |
| (5) | Sodium hydroxide | 7.5 |
| (6) | Palm oil fatty acid amidopropyl betaine | 1.0 |
| (7) | Purified water | 36.5 |
| (8) | Extract of *Hibiscus makinoi* (Production Example 2) | 1.0 |

Production method: oil phase components of (1) to (4) are dissolved by heating at 80° C. On the other hand, aqueous phase components of (5) to (7) are dissolved by heating at 80°

C., and uniformly mixed with the oil phase components by stirring. Cooling is initiated, and (8) is added at 40° C. and uniformly mixed.

Prescription Example 8

Makeup Base Cream

TABLE 20

| | Components | Amount (mass %) |
|---|---|---|
| (1) | Squalan | 10.0 |
| (2) | Cetanol | 2.0 |
| (3) | Glycerin tri-2-ethylhexane acid ester | 2.5 |
| (4) | Lipophilic type glyceryl monostearate | 1.0 |
| (5) | Propylene glycol | 11.0 |
| (6) | Sucrose fatty acid ester | 1.3 |
| (7) | Purified water | 69.4 |
| (8) | Titanium oxide | 1.0 |
| (9) | Colcothar | 0.1 |
| (10) | Yellow iron oxide | 0.4 |
| (11) | Fragrance | 0.1 |
| (12) | Extract of *Hibiscus makinoi* (Production Example 1) | 1.2 |

Production method: oil phase components of (1) to (4) are mixed, and dissolved by heating at 75° C. On the other hand, aqueous phase components of (5) to (7) are mixed, and dissolved by heating at 75° C., and thereto are added pigments of (8) to (10), and uniformly dispersed by a homomixer. The above oil phase components are added to this aqueous phase components, and emulsified by a homomixer. After completion of the emulsification, cooling is initiated, and the components of (11) and (12) are added at 40° C. and uniformly mixed.

Prescription Example 9

Milky Foundation

TABLE 21

| | Components | Amount (mass %) |
|---|---|---|
| (1) | Methylpolysiloxane | 2.0 |
| (2) | Squalan | 5.0 |
| (3) | Octyldodecyl myristate | 5.0 |
| (4) | Cetanol | 1.0 |
| (5) | Polyoxyethylene (20E.O.) sorbitan monostearate ester | 1.3 |
| (6) | Sorbitan monostearate | 0.7 |
| (7) | 1,3-butylene glycol | 8.0 |
| (8) | Xanthan gum | 0.1 |
| (9) | Methyl paraoxybenzoate | 0.1 |
| (10) | Purified water | 57.4 |
| (11) | Titanium oxide | 9.0 |
| (12) | Talc | 7.4 |
| (13) | Colcothar | 0.5 |
| (14) | Yellow iron oxide | 1.1 |
| (15) | Black iron oxide | 0.1 |
| (16) | Fragrance | 0.1 |
| (17) | Extract of *Hibiscus makinoi* (Production Example 2) | 1.0 |

Production method: Oil phase components of (1) to (6) are mixed, and dissolved by heating at 75° C. On the other hand, aqueous phase components of (7) to (10) are mixed, and dissolved by heating at 75° C., and thereto are added pigments of (II) to (15), and uniformly dispersed by a homomixer. The oil phase components are added and emulsified. After completion of the emulsification, cooling is initiated, and the components of (16) and (17) are sequentially added at 40° C. and uniformly mixed.

Prescription Example 10

Water-in-Oil Type Emollient Cream

TABLE 22

| | Components | Amount (mass %) |
|---|---|---|
| (1) | Fluid paraffin | 30.0 |
| (2) | Micro crystalline wax | 2.0 |
| (3) | Vaseline | 5.0 |
| (4) | Diglycerin oleic acid ester | 5.0 |
| (5) | Sodium chloride | 1.3 |
| (6) | Potassium chloride | 0.1 |
| (7) | Propylene glycol | 3.0 |
| (8) | 1,3-butylene glycol | 5.0 |
| (9) | Methyl paraoxybenzoate | 0.1 |
| (10) | Extract of *Hibiscus makinoi* (Production Example 2) | 1.0 |
| (11) | Purified water | 47.4 |
| (12) | Fragrance | 0.1 |

Production method: (5) and (6) are dissolved in a part of (11) and adjusted at 50° C., and the mixture is gradually added to (4) that is heated at 50° C. while stirring. After mixing these components, the mixture is uniformly dispersed in (1) to (3) dissolved by heating at 70° C. Thereto are added (7) to (10) that are dissolved in the residue of (11) by heating at 70° C. while stirring, and emulsified by a homomixer. After completion of the emulsification, cooling is initiated, and (12) is added at 40° C. and uniformly mixed.

Prescription Example 11

Facial Mask

TABLE 23

| | Components | Amount (mass %) |
|---|---|---|
| (1) | Purified water | 58.9 |
| (2) | Polyvinyl alcohol | 12.0 |
| (3) | Ethanol | 17.0 |
| (4) | Glycerin | 5.0 |
| (5) | Polyethylene glycol (average molecular weight 1000) | 2.0 |
| (6) | Extract of *Hibiscus makinoi* (Production Example 1) | 5.0 |
| (7) | Fragrance | 0.1 |

Production method: (2) and (3) are mixed and heated at 80° C., and dissolved in (1) that is heated at 80° C. After uniformly dissolving, (4) and (5) are added, and cooling is initiated while stirring. The mixture is cooled to 40° C., and (6) and (7) are added thereto and uniformly mixed.

Prescription Example 12

Bath Salt

TABLE 24

| | Components | Amount (mass %) |
|---|---|---|
| (1) | Fragrance | 0.3 |
| (2) | Extract of *Hibiscus makinoi* (Production Example 2) | 1.0 |
| (3) | Sodium hydrogen carbonate | 50.0 |
| (4) | Sodium sulfate | 48.7 |

Production method: (1) to (4) are uniformly mixed.

Prescription Example 13

Hair Wax

TABLE 25

| | Components | Amount (mass %) |
|---|---|---|
| (1) | Stearic acid | 3.0 |
| (2) | Micro crystalline wax | 2.0 |
| (3) | Cetyl alcohol | 3.0 |
| (4) | Highly-polymerized methylpolysiloxane | 2.0 |
| (5) | Methylpolysiloxane | 5.0 |
| (6) | Poly(oxyethylene/oxypropylene) methylpolysiloxane copolymer | 1.0 |
| (7) | Methyl paraoxybenzoate | 0.1 |
| (8) | 1,3-butylene glycol | 7.5 |
| (9) | Arginine | 0.7 |
| (10) | Purified water | 73.6 |
| (11) | Extract of *Hibiscus makinoi* (Production Example 2) | 2.0 |
| (12) | Fragrance | 0.1 |

Production method: Oil phase components of (1) to (6) are mixed and dissolved by heating at 75° C. On the other hand, aqueous phase components of (7) to (10) are dissolved by heating at 75° C., and the above oil phase components are added thereto and emulsified by a homomixer. After completion of the emulsification, cooling is initiated, and the components of (11) and (12) are added at 40° C. and uniformly mixed.

Prescription Example 14

Hair Tonic

TABLE 26

| | Components | Amount (mass %) |
|---|---|---|
| (1) | Ethanol | 50.0 |
| (2) | Purified water | 48.9 |
| (3) | Extract of *Hibiscus makinoi* (Production Example 1) | 1.0 |
| (4) | Fragrance | 0.1 |

Production method: The components of (1) to (4) are mixed and homogenized.

Prescription Example 15

Beverage

TABLE 27

| | Components | Amount (mass %) |
|---|---|---|
| (1) | Extract of *Hibiscus makinoi* (Production Example 1) | 8.0 |
| (2) | Erythritol | 1.0 |

TABLE 27-continued

| | Components | Amount (mass %) |
|---|---|---|
| (3) | Citric acid | 0.1 |
| (4) | *Stevia* | 0.0 |
| (5) | Purified water | 90.9 |

Production method: (1) to (5) are uniformly mixed.

As illustrated above, according to the present invention, a cell activation agent, a collagen production accelerator, a whitening agent, an antioxidant, an anti-inflammatory agent, an aromatase activity accelerator, and a protease activity accelerator, which have excellent effects, can be provided. Further, blending an extract of *Hibiscus makinoi* in a skin external preparation allows to provide an anti-aging improving skin external preparation exerting an excellent effect in prevention and improvement of skin aging symptoms such as wrinkles, sagging, skin tension, spots and somberness, a whitening skin external preparation exerting an excellent effect in melanin production suppression, and an anti-inflammatory skin external preparation exerting an excellent anti-inflammatory effect. Furthermore, by blending an extract of *Hibiscus makinoi* in food, beverage and medical products, food, beverage and medical products exerting an excellent effect in beautification, health maintenance and nutritional support can be provided.

INDUSTRIAL APPLICABILITY

According to the present invention, a cell activation agent, a collagen production accelerator, a whitening agent, an antioxidant, an anti-inflammatory agent, an aromatase activity accelerator, and a protease activity accelerator, which have excellent effects, can be provided. Further, blending an extract of *Hibiscus makinoi* in a skin external preparation allows to provide an anti-aging improving skin external preparation exerting an excellent effect in prevention and improvement of skin aging symptoms such as wrinkles, sagging, skin tension, spots and somberness, a whitening skin external preparation exerting an excellent effect in melanin production suppression, and an anti-inflammatory skin external preparation exerting an excellent anti-inflammatory effect. Furthermore, by blending an extract of *Hibiscus makinoi* in food, food exerting an excellent effect in beautification, health maintenance, and nutritional support can be provided.

The invention claimed is:

1. A cell activation agent characterized by comprising an extract of *Hibiscus makinoi*.
2. A collagen production accelerator characterized by comprising an extract of *Hibiscus makinoi*.
3. A whitening agent characterized by comprising an extract of *Hibiscus makinoi*.
4. An antioxidant characterized by comprising an extract of *Hibiscus makinoi*.
5. An anti-inflammatory agent characterized by comprising an extract of *Hibiscus makinoi*.
6. An aromatase activity accelerator characterized by comprising an extract of *Hibiscus makinoi*.
7. A protease activity accelerator characterized by comprising an extract of *Hibiscus makinoi*.
8. A skin external preparation characterized by comprising an extract of *Hibiscus makinoi*.
9. Food characterized by comprising an extract of *Hibiscus makinoi*.

* * * * *